United States Patent [19]

Babbitt et al.

[11] Patent Number: 5,002,736

[45] Date of Patent: Mar. 26, 1991

[54] MICROSCOPE SLIDE AND SLIDE ASSEMBLY

[75] Inventors: Thomas J. Babbitt, York, Me.; David J. Brigati, Hummelstown, Pa.

[73] Assignees: Fisher Scientific Co., Pittsburgh, Pa.; Erie Scientific Co., Portsmouth, N.H.

[21] Appl. No.: 112,404

[22] Filed: Oct. 26, 1987

Related U.S. Application Data

[63] Continuation-in-part of Ser. No. 33,073, Mar. 31, 1987, Pat. No. 4,777,020, which is a continuation-in-part of Ser. No. 775,864, Sep. 13, 1985, Pat. No. 4,731,335.

[51] Int. Cl.⁵ ............................................... B01L 1/00
[52] U.S. Cl. ..................................... 422/100; 422/99; 422/102; 350/534; 428/210; 73/864
[58] Field of Search .............. 422/99, 102, 101, 100; 350/534–536; 428/210; 73/864

[56] References Cited

U.S. PATENT DOCUMENTS

| | | | |
|---|---|---|---|
| 2,863,319 | 12/1958 | McLin | 73/425.4 |
| 4,022,521 | 5/1977 | Hall et al. | 350/95 |
| 4,447,140 | 5/1984 | Campbell et al. | 350/534 |
| 4,481,246 | 11/1984 | Melisz et al. | 350/534 |
| 4,596,695 | 6/1986 | Cottingham | 422/58 |
| 4,624,882 | 11/1986 | Melisz et al. | 350/534 |
| 4,647,543 | 3/1987 | Stocker | |
| 4,677,543 | 3/1987 | Stocker | 436/174 |
| 4,679,914 | 7/1987 | Rosenberg | 350/534 |
| 4,761,381 | 8/1988 | Blatt et al. | 422/102 |
| 4,777,020 | 10/1988 | Brigati | 422/99 |

FOREIGN PATENT DOCUMENTS

| | | |
|---|---|---|
| 117262 | 5/1984 | European Pat. Off. . |
| 2180647 | 4/1987 | United Kingdom . |

*Primary Examiner*—Robert J. Hill, Jr.
*Assistant Examiner*—Lyle Alfandary-Alexander
*Attorney, Agent, or Firm*—Alan M. Doernberg

[57] ABSTRACT

Two rectangular slides having front and rear faces are held with front faces facing each other. Raised end portions on one or both front faces abut and space the front faces by a distance (e.g., 100 to 250 μm) conducive for reversible capillary action between the slides. Raised island portions on one or both front faces are located at corners opposite the raised end portions. The raised island portions serve to maintain spacing between the front faces, particularly as the ends of the slides opposite to the raised end portions contact an absorbent material. An opening between the raised island portions permits liquid to enter and leave the gap between the front faces.

14 Claims, 2 Drawing Sheets

MICROSCOPE SLIDE AND SLIDE ASSEMBLY

This is a continuation-in-part of U.S. Ser. No. 033,073 of David J. Brigati entitled, "Sheetlike Object Such As Microscope Slide", filed Mar. 31, 1987 and copending, now U.S. Pat. No. 4,777,020, issued Oct. 11, 1988, which was a continuation-in-part of U.S. Ser. No. 775,864, filed Sept. 13, 1985 now U.S. Pat. No. 4,731,335.

Microscope slides are typically rectangular glass objects having front and back faces or surfaces of a length (height) such as 75 mm or three inches (76.2 mm) and of a width such as 25 mm or one inch (25.4 mm). Such slides are made in a variety of thicknesses such as 0.9, 1.0 or 1.2 mm. It is common to frost part or all of the front face of the slide for a variety of purposes such as enabling the user to write sample identifying information on the slide. For such frosting or other reasons, a portion of the front face may be roughed or carved into. Other portions of the front face of the slide may remain sufficiently flat to be optically clear.

A partially coated slide described in U.S. Pat. Nos. 4,481,246, 4,624,882 and 4,679,914 and typically sold under the SUPERFROST registered trademark has a polymeric coating of thickness under 20 microns (20 um) at an end on the surface of the slide (e.g., the end 10 mm).

In application U.S. Ser. No. 775,864 (see GB No. 2,180,647, published Apr. 1, 1987), now U.S. Pat. No. 4,731,335 Brigati describes modified microscope slides used in a method involving capillary action. Two microscope slides are arranged with front faces or surfaces opposite and held with such faces separated by a capillary gap (e.g., of about 50-500 um thickness). Such a gap is defined in some disclosed embodiments by a shim (tape or cover slip) fastened or held between the top portions of the opposite front faces. In another disclosed embodiment, the gap is defined by a coating on one of the slides.

BRIEF DESCRIPTION

In the course of further developing slide pairs and slides for capillary action methods based upon the invention of U.S. Ser. No. 775,864, a problem has been recognized and overcome involving the stability of the capillary gap. The solution has involved a coating on one or both front slide faces near a common end (typically the top end) and island coatings on the corners of the opposite end (typically the bottom left and bottom right corners) of one or both slides of the slide pair. The total thickness of end coatings should be a thickness desirable for reversible capillary action (e.g., about 50-500 um), but the total thickness of the island coatings can be either smaller, larger or (preferably) in the same range.

Accordingly, the present invention provides a microscope slide assembly comprising a first substantially rectangular slide having front and back faces and a second substantially rectangular slide having front and back faces, an end portion of the front face of at least one of the first and second slides having a raised portion of thickness about 50 to 500 um separating the front faces of the first and second slides by the thickness of the raised portion and a pair of raised islands being disposed at the corners of at least one of the first and second slides distal from the end portion.

The present invention further provides a microscope slide having a front face and a raised portion on one end of the front face of thickness about 25 to 500 um and a pair of raised island portions on the corners of the front face distal from the one end.

DETAILED DESCRIPTION

Figure 1:
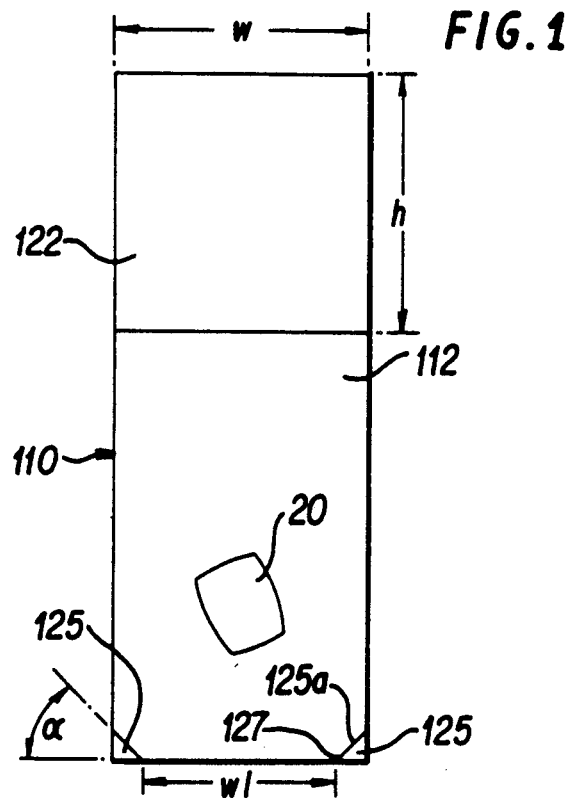
Figure 2:
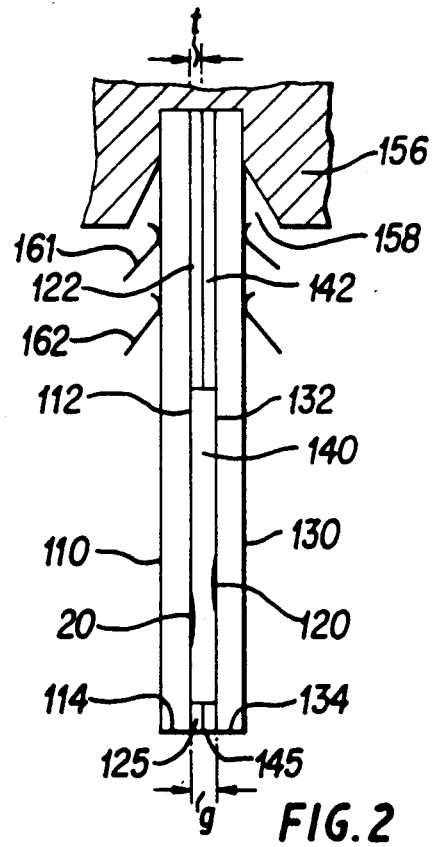

In FIG. 1, a microscope slide 110 according to a first embodiment of the present invention is shown. The front face 112 of the slide 110 has a tissue specimen 20 centered from left to right and placed on the lower one-third of the slide 110. A top coating 122 covers a portion of the front face of the slide (e.g., the top 31.8 mm out of a total height of 76.2 mm). Small triangular coating poritions or raised islands 125 cover the bottom left and right corners of the front face of slide 110. Each of these coatings are one-half the thickness of the desired gap of a slide assembly as illustrated in FIG. 2 (e.g., each coating being 80 um thick to form a 160 um thick gap). The sample 20 of tissue is positioned on slide 110 below coating 122, but above both the raised islands 125 and lower edge 114 of slide 110.

Representative dimensions for coating 122 are 31.8 mm high h, 25.4 mm wide w (the full width of slide 110) and 0.08 mm (80 um) thick t. Significant variations in height h and width w are permissable and, as described below, the the thickness t can be 25-250 um. Representative dimensions for triangular coating portions 125 (raised islands) are 4 mm maximum height (along the outer left and right edges of slide 110), 4 mm maximum width (along bottom edge 114) and 80 um thickness. Substantial variations in the height and general shape of the raised islands 125 are permissable (as described more fully below in connection with FIGS. 4A, 4B, and 4C); nevertheless it is preferred that each raised island extend from each corner inwardly along bottom edge 114 and upwardly along a side edge of slide 110.

FIG. 2 is a side view of two identical slides 110 and 130 in a slide holder. Slides 110 and 130 together form a slide assembly when held together as shown in FIG. 2. The coating 122 on slide 110 abuts against identical top coating 142 on slide 130. Bottom corner coating 125 on slide 110 abuts against bottom corner coating 145 in slide 130. Slides 110 and 130 are pressed together by clips 161 and 162 which are, respectively, above and below the midpoint of coatings 122 and 142. Tops of slides 110 and 130 are received within a slot 158 of alignment strip 156 of a slide holder described in copending application U.S. Ser. No. 032,874 of Brigati and Cuomo, filed Mar. 31, 1987, the disclosure of which is incorporated herein by reference. The horizontally-extending surface of the slot 158 maintains precise vertical alignment between slides 110 and 130. For the holder described in application Ser. No. 032,874, slots are provided near each of the two top corners of slides 110 and 130 and side walls are provided to maintain horizontal alignment between slides 110 and 130 in a direction into the page in the view of FIG. 2. In such slide holder, each alignment strip has multiple slots (illustrated as ten) so that multiple (ten) slide pairs can be held in a fixed array.

Because each of coatings 122, 125, 142 and 145 is about 80 micrometers thick, the 160 micrometer thick gap 140 is maintained, but flares out at a 45 degree angle alpha from a width wl of 17.4 mm at the lower edge of a width w of 25.40 mm at a height of 40 mm above such lower edge (see FIG. 1).

Figure 3A:
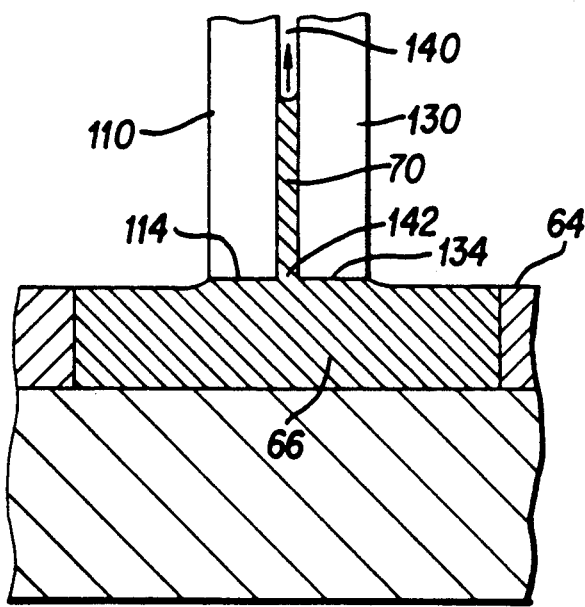
Figure 3B:
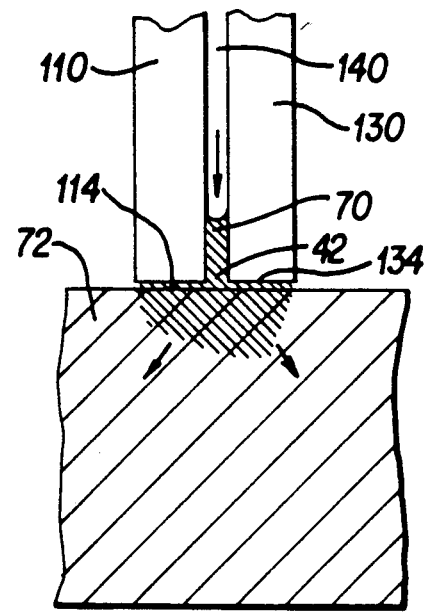

In use, up to thirty slide pairs (with samples on one or both slide of each pair) are inserted into the holder. The holder is then lowered onto a series of liquids, typically liquid reagents. Each liquid may be in the form of a bath or sheet, in the form if individual round droplets supported on a droplet holder (see FIG. 7 of U.S. Ser. No. 775,884) or in the form of laterally-extending aliquots on a modified droplet holder (see FIGS. 3A, 3B and 3C of an application of Brigati, U.S. Ser. No. 032,875, filed Mar. 31, 1987, and also a continuation-in-part of U.S. Ser. No. 775,884the disclosure of which is incorporated herein by reference). Liquid rises by capillary action into the gap 140 between each first slide 110 and the adjacent second or facing slide 130. See FIG. 3A hereof. After the appropriate time of liquid contacting sample on one or both slides, the slide assembly is then lowered on a flat blotter 72. Liquid is then drawn by capillary action into the blotter 72 so as to evacuate each capillary gap 140, as shown in FIG. 3B hereof. If a droplet holder is used for the particular step, then the process can be individualized so as to treat different slide pairs with different liquides (e.g., different primary antibodies, nucleic acid probes, enzymes or chromogens). After evacuation, the slide assembly can then be contacted by another reagent in the form of droplets, laterally-extending aliquots or a sheet or bath of liquid. Looking at FIG. 3A, a liquid droplet is in hole 66 through elastomeric member 64 on rigid base 62. The lower edges 114 and 134 of slides 110 and 130, respectively, contact the top of the droplet so that the lower edge 142 of gap 140 also,contacts the droplet. A rising column of liquid 70 is drawn upward into the gap 140 by capillary action as described more fully in application Ser. No. 775,884, filed Sept. 13, 1985, copending (see also GB No. 2,180,647 A, published Apr. 1, 1987), the disclosure of which is incorporated herein by reference.

Looking at FIG. 3B, the lower edges 114 and 134 of slides 110 and 130 contact, at the end of a treating or washing step, a blotter 72 of absorbent material. The liquid is then drawn by capillary action out of gap 140 through its lower edge 42 into blotter 72, where it forms a downwardly and outwardly spreading liquid front 74, causing the column 70 of liquid in gap 140 to fall.

In the course of multiple treatment steps, the pair of slides 110 and 130 is repeatedly contacted with sources of treating liquids (some of which may be discrete droplets as in hole 66) and blotters such as blotter 72. Looking at FIGS. 2 and 3B, it should be appreciated that coatings 122 and 132, coupled with the rigidity of slides 110 and 130, will usually, but not always, suffice to maintain the thickness of the gap 140 between lower edges 114 and 134 constant. In particular, when lower edges 114 and 134 are pressed down into blotter 72, the blotter 72 will tend to press edges 114 and 134 of slides 110 and 130 together. Such pressure is likely to occur when the resistance of edges 114 adn 134 against blotter 72 is relied upon to stop the downward motion of the array of slides as is the case with current models of Fisher Scientific Company's HISTOMATIC slide stainer, CODE-ON version, which employs a solenoid mechanism to stop downward movement when the slide array encounters a resistance.

By providing raised islands 125 and 145 (as seen in FIG. 2), edges 114 and 134 are prevented from coming together to close lower edge 42 of gap 140. The triangular shape of islands 125 and 145 is ideal for maintaining the spacing between lower edges 114 and 134 without islands 125 and 145 themselves sealing off any appreciable portion of gap 140 (i.e., only the outer 4 mm on each side of a 25.4 mm gap, leaving the central 17.4 mm open). During filling of the gap (as shown in FIG. 3A) the rising column 70 easily broadens from the smaller width wl at lower edge 42 (17.4 mm) to the full width w (25.4 mm) at the top of islands 125 and 145 (4 mm above lower edges 114, 42 and 134). During evacuation of the gap (as shown in FIG. 3B), the falling column 70 easily narrows from the full width w (25.4 mm) at the top of islands 125 and 145 to the narrower width wl (17.4 mm) at lower edge 42. The angled edge 127 of islands 125 and 145 (forming an acute angle alpha of 45 degrees with the lower edges 114 and 134, respectively) does not hold up residual liquid at the end of the evacuation step.

Figure 4A:
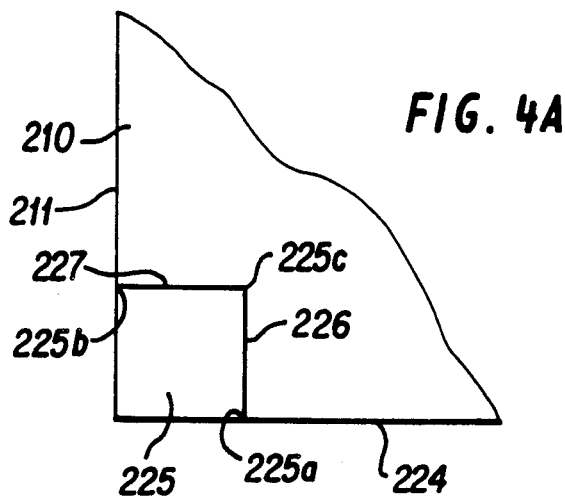

FIG. 4A illustrates a modified slide according to a second embodiment of the present invention, looking at the bottom left corner (the bottom right corner would be a mirror image). Raised island 225 is at the bottom left corner of slide 210, with its lower edge extending from the corner along lower edge 214 of slide 210. Because raised island 225 is square in shape (e.g., 4 mm by 4 mm), its bottom right side 226 forms a 90 degree angle 225a with lower edge 214, its upper left side 227 forms a 90degree angle 225a with the left edge 211 of slide 210 and its side 227 forms another 90 degree angle 225c with side 226.

When two modified slides 210 are maintained in face-to-face alignment (as with slides 110 and 130 in FIGS. 2, 3A and 3B), the slide pair can be used to draw in treating liquid and evacuate treating liquid into a blotter as described above. The facing islands 225 will prevent the lower end of the gap from closing and will not interfere at all with the rising column of liquid during the drawing of liquid into the gap. During evacuation, substantially all of the liquid will be evacuated from the gap (except of course that liquid which is absorbed into or adsorbed onto the sample), but some small amount of liquid may remain on top of each raised island 225 (i.e., on top of the horizontal edge 227 between angles 225b and 225c).

Figure 4B:
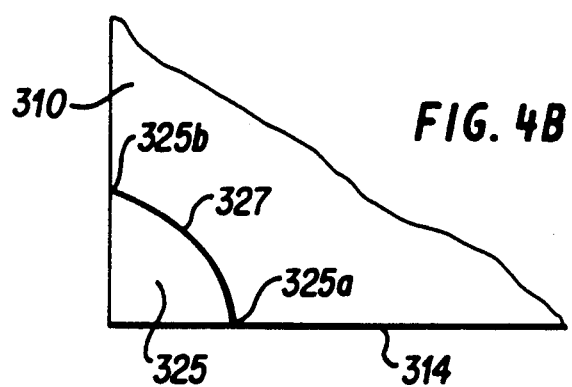

The bottom left corner of a microscope slide 310 according to a third embodiment of the present invention is illustrated in FIG. 4B. Raised island 325 extends upwardly from the lower edge 314 of slide 310. Raised island 325 has the shape (profile) of a quarter circle, with a curved edge 327 extending between point 325b on the left edge of slide 310 and point 325a on the lower edge 314 of slide 310. The convex shape of this curved portion 327 (and of the corresponding portion of the mirror-image island on the bottom right of the front face of slide 310) should enable two slides 310, when held in face-to-face alignment, to be evacuated more completely than two slides 210 (as shown in FIG. 4A) when held in similar face-to-face alignment, and to be evacuated as completely, or almost as completely, as slides 110 and 130, as shown in FIGS. 2, 3A and 3B.

Figure 4C:
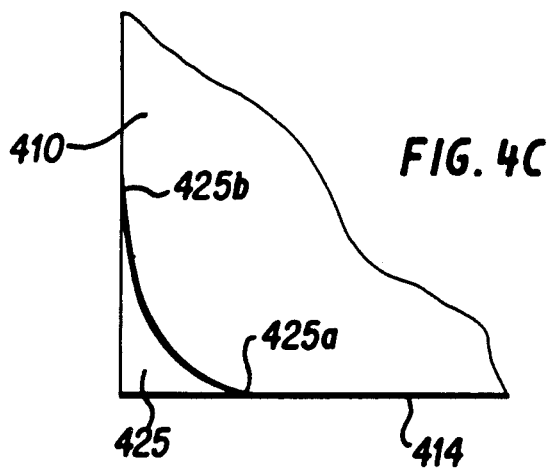

FIG. 4C illustrates the bottom left corner of a slide 410 according to a fourth embodiment of the present invention. The generally convex shape of the portion of raised island 425 between points 425b and 425a should facilitate complete evacuation of the gap between two face-to-face slides 410.

Figure 5:
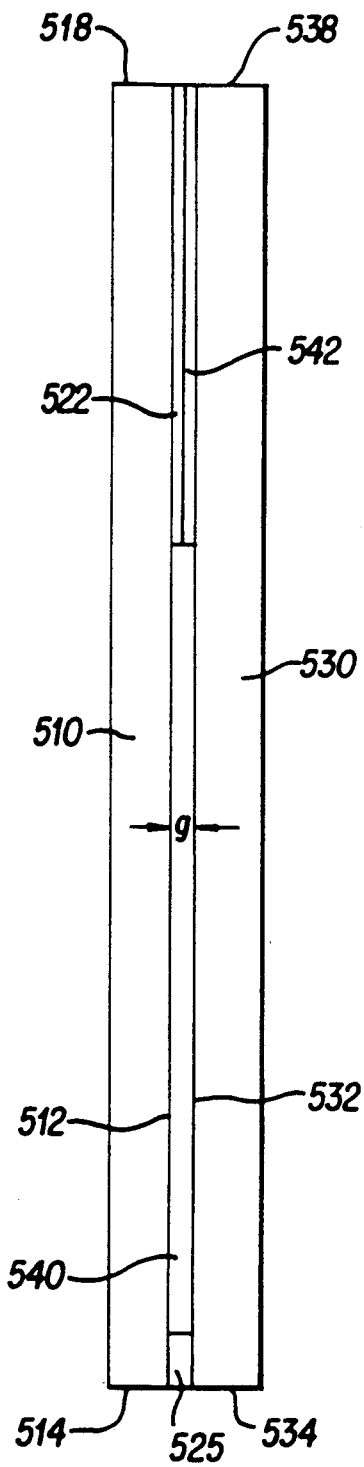

FIG. 5 illustrates, in side view, two face-to-face slides 510 and 530. The front face 512 of slide 510 extends from the top edge 518 to the bottom edge 514, with about the top 40% of front face 512 being coated by raised portion 522 of slide 530 extends from top edge 538 to bottom edge 534, with the top one-third of front face 532 being coated with a raised portion 542 (e.g., of thickness 80 um). Instead of having raised islands on the bottom corners of both slide 510 and slide 530, a single pair of raised islands 525 (only one of which is visible in this side view) is formed at and above the bottom edge 514 of slide 510. A gap 540 of uniform thickness g of approximately 160 um between faces 512 and 532 can be maintained by forming raised islands 525 with a thickness of 160 um rather than 80 um. It is entirely suitable, however, for raised islands 525 to be of a different thickness than the sum of the thicknesses of raised portions 522 and 542. It is also entirely suitable to have raised portion 522, raised portion 542 and raised islands 525 each be of a different thickness (such as 75 um, 100 um and 150 um, respectively) in order to facilitate the fabrication of slides 510 and 530 without materially altering the thickness g of the gap 540.

In each of the various embodiments, the sum of the thicknesses of the abutting raised end portions (top coatings) may range generally between about 50 and about 500 um, but is preferably between about 75 and about 250 um, more preferably between about 100 and about 250 um and most preferably between about 100 and about 200 um. In certain cases, the preferred range is about 75 to about 200 um, especially about 75 to about 150 um, when particularly smooth glass is used and longer evacuation times are acceptable. The same ranges apply to individual slides which are to be used in conjunction with slides without raised end portions (e.g., conventional flat microscope slides). It is preferred, however, to have raised end portions on both slides in a facing pair, whose thicknesses may be the same or different. For the most common case in which facing slides have raised end portions of identical thicknesses (as would be the case if the slides were in all respects identical), the raised end portion on each slide could be about 25 to about 250 um thick, but would preferably be about 38 to about 125 um thick, more preferably about 50 to about 125 um thick and most preferably about 50 to about 100 um thick. It is not necessary, however, for each raised end portion (top coating) to be of uniform thickness, with the above thickness applying to the thickest portion of the top coating on a slide, provided that it would abut the top coating, if any of the facing slide. Such thickest portion would normally comprise the majority of the area of the top coating in those cases where the top coating is not of uniform thickness. As a general rule, too much thickness produces a gap too thick to draw liquid in efficiently, while too little thickness produces a gap too thin for liquid to be easily drawn out by capillary action. The various preferred thicknesses of raised portions of individual slides and of slide assemblies are designed with this feature in mind. From a fabrication standpoint, it is easiest to form a raised portion on an individual slide of 10 to 125 um.

Corresponding preferred, more preferred and most preferred ranges apply to the island portions of each slide and of the slide pair. It is suitable, however, for the facing island portions to contain less than 50 um total thickness, although this is not preferred. In general the sum of the thicknesses of the island portions of a slide pair should be reasonably proportioned relative to the sum of the thicknesses of the raised end portions of the same slide pair (e.g., between 66% and 150% of such sum) in order not to form a capillary gap that slants excessively from top to bottom. As pointed out by FIG. 5, however, that reasonable proportioning of the two sums does not preclude the island portions on an individual slide being much thicker than the raised end portions on the same slide.

A variety of techniques are contemplated to form both the raised portions (122, 142, 122, 322, 422, and 522 in various Figures) and the raised islands (125, 145, 225, 325, 425, and 525 in various figures) on slides. The base slide material is normally optical quality glass, but clear plastic may also be used. Optically opaque surfaces such as plastic, metal or elastomers can be used in certain applications. In the event that the raised portions and raised islands are to be formed by coating, various thermoplastic, thermosetting or resinous materials may be used and applied in the form of a paint, melt or ink.

In the event that a coating process is used, one or more layers may be applied. In some forms, colors are selected for individual layers that will assist in identifying either particular slides or the front or back faces of particular slides. Thus, for example, all slides associated with a particular slides. Thus, for example, all slides associated with a particular test could have blue and white coating layers, but the control slides could have white corner spots and the sample slides have blue corner spots. Furthermore, the frontmost coating layer that forms raised portion 122 could be blue, while the rearmost layer could be white.

It is also suitable to coat the surfaces of the slides which are in contact with the capillary gap with coatings such as gelatin, albumin or serum in order to increase the rate of capillary action during both filling and evacuation of the gap.

We claim:

1. A microscope slide assembly comprising a first substantially rectangular slide having front and back faces and a second substantially rectangular slide having front and back faces, the first and second slides being arranged substantially in parallel in the slide assembly with the front face of the first slide being adjacent to and facing the front face of the second slide and with the four corners of the first slide each being adjacent to a corresponding corner of the second slide, an end portion of the first or second slide having a raised portion of thickness 50 to 500 um engaging and separating the front faces of the first and second slides by the thickness of the raised portion; and a pair of raised island of thickness 50 to 500 um being disposed between the first and second slides at each of the two facing corners of the first and second slides distal from the end portion where the raised portion is formed, each raised island being separated from the raised portion and from the raised island at the other corner.

2. The microscope slide assembly of claim 1 further comprising means for holding the first and second slides in a front face to front face relationship.

3. The microscope slide assembly of claim 1 wherein the raised portion and raised islands are each formed on the first slide.

4. The microscope slide assembly of claim 3 wherein the raised islands are of right triangular shape and have edges substantially aligned with edges of the first and second slides.

5. The microscope slide assembly of claim 1 wherein the raised portion comprises a first raised portion on the front face of the first slide and a second raised portion on the front face of the second slide wherein the raised portions of the first and second slides have a total thickness of about 75 to about 250 um.

6. The microscope slide assembly of claim 5 wherein said total thickness is about 100 to about 250 um.

7. The microscope slide assembly of claim 1 wherein the raised portion comprises a first raised portion on the front face of the first slide and a second raised portion on the face of the second slide of substantially equal thickness to that of the first raised portion and the pair of raised islands comprise a first pair on the face of the first slide and a second pair on the face of the second slide wherein each island has substantially equal thickness.

8. The microscope slide assembly of claim 7 wherein the thickness of the raised portions on each of the first and second slides is about 38 to about 125 um.

9. A microscope slide having a front face and a raised portion on one end of the front face of thickness 25 to 500 um and a pair of raised island portions on the corners of the front face distal from the one end, each raised island portion being of thickness 25 to 500 um and being separated from the raised portion and from the other raised island portion.

10. The microscope slide of claim 9 wherein said raised portion has a thickness of about 50 to about 125 um.

11. The microscope slide of claim 10 wherein each raised island portion has a thickness of about 66% to about 150% of the thickness of the raised portion.

12. A substantially rectangular slide for use in a slide assembly comprising two slides face to face, said slide having a front face and rear face, said front face having a raised portion at one end thereof and a pair of raised islands located at the opposite end from said raised portion, said raised portion and said pair of raised islands having a thickness of 10 to 250 um, each raised island being separated from said raised portion and from the other raised island.

13. The slide of claim 12 wherein said raised portion and said pair of raised islands have a thickness of 25 to 125 um.

14. The slide of claim 13 wherein said raised portion and said pair of raised islands have a thickness of 38 to 100 um.

* * * * *